(12) United States Patent
Honda et al.

(10) Patent No.: US 10,102,730 B2
(45) Date of Patent: Oct. 16, 2018

(54) MONITORING APPARATUS FOR MONITORING A TARGETS EXPOSURE TO DANGER

(71) Applicant: FUJI XEROX CO., LTD., Tokyo (JP)

(72) Inventors: Hiroshi Honda, Kanagawa (JP); Takanori Ozawa, Kanagawa (JP); Kazuaki Morito, Kanagawa (JP); Manabu Hayashi, Kanagawa (JP)

(73) Assignee: FUJI XEROX CO., LTD., Tokyo (JP)

( * ) Notice: Subject to any disclaimer, the term of this patent is extended or adjusted under 35 U.S.C. 154(b) by 0 days.

(21) Appl. No.: 15/479,671

(22) Filed: Apr. 5, 2017

(65) Prior Publication Data

US 2018/0165938 A1    Jun. 14, 2018

(30) Foreign Application Priority Data

Dec. 9, 2016 (JP) ................. 2016-239762

(51) Int. Cl.

| G08B 21/02 | (2006.01) |
| G08B 21/04 | (2006.01) |
| G08B 21/18 | (2006.01) |
| A61B 5/11 | (2006.01) |
| G06K 9/00 | (2006.01) |
| G08B 21/22 | (2006.01) |

(52) U.S. Cl.
CPC ........ *G08B 21/0476* (2013.01); *A61B 5/1113* (2013.01); *A61B 5/1115* (2013.01); *A61B 5/1128* (2013.01); *G06K 9/00664* (2013.01); *G06K 9/00671* (2013.01); *G06K 9/00771* (2013.01); *G08B 21/02* (2013.01); *G08B 21/0438* (2013.01); *G08B 21/0469* (2013.01); *G08B 21/0492* (2013.01); *G08B 21/182* (2013.01); *G08B 21/22* (2013.01)

(58) Field of Classification Search
CPC .......... G06K 9/00664; G06K 9/00671; G06K 9/00771; A61B 5/1115; A61B 5/1113; A61B 5/1128; G08B 21/0476; G08B 21/182; G08B 21/22; G08B 21/0483; G08B 21/0446; G08B 21/0469; G08B 21/0492; G08B 21/02; G08B 21/0438
See application file for complete search history.

(56) References Cited

U.S. PATENT DOCUMENTS

| 4,947,152 A * | 8/1990 | Hodges | G08B 21/22 340/286.07 |
| 6,796,799 B1 * | 9/2004 | Yoshiike | G06F 19/3418 434/236 |

(Continued)

FOREIGN PATENT DOCUMENTS

| JP | 2005-352881 A | 12/2005 |
| JP | 2006-145485 A | 6/2006 |
| JP | 2014-174627 A | 9/2014 |

*Primary Examiner* — Andrew Bee
(74) *Attorney, Agent, or Firm* — Oliff PLC

(57) ABSTRACT

A monitoring apparatus includes a detector and a notifying unit. The detector detects, based on an image obtained by capturing an image of a space in which a monitoring target acts, an act which is likely to cause the monitoring target to be exposed to danger. The notifying unit sends, in accordance with the act and an exercise ability of the monitoring target, a notification indicating that the monitoring target is likely to be exposed to danger.

17 Claims, 11 Drawing Sheets

(56) References Cited

U.S. PATENT DOCUMENTS

| | | | |
|---|---|---|---|
| 6,968,294 B2 * | 11/2005 | Gutta | A61B 5/7264 |
| | | | 600/595 |
| 7,319,386 B2 * | 1/2008 | Collins, Jr. | A61B 5/1115 |
| | | | 340/286.07 |
| 7,987,069 B2 * | 7/2011 | Rodgers | A61B 5/1115 |
| | | | 340/573.1 |
| 9,396,543 B2 * | 7/2016 | Uetsuji | G06T 7/0051 |
| 2003/0058111 A1 * | 3/2003 | Lee | G06K 9/00342 |
| | | | 340/573.1 |
| 2013/0127620 A1 * | 5/2013 | Siebers | G08B 21/02 |
| | | | 340/573.1 |
| 2013/0184592 A1 * | 7/2013 | Venetianer | H04N 7/18 |
| | | | 600/476 |
| 2014/0253710 A1 * | 9/2014 | Yasukawa | A61B 5/1128 |
| | | | 348/77 |
| 2016/0371950 A1 * | 12/2016 | Yasukawa | A61B 5/1115 |

* cited by examiner

FIG. 3

| LOCATION OF DANGEROUS PLACE | DEGREE OF DANGEROUSNESS | DANGEROUS TARGET |
|---|---|---|
| $(x_1, y_1)$ | 4 cm | STEP |
| $(x_2, y_2), (x_3, y_3)$ $(x_4, y_4), (x_5, y_5)$ | 5 cm | CABLE OF 1 METER LONG |

| AVERAGE DAILY NUMBER OF STEPS (STEPS/DAY) | WALKING ABILITY LEVEL | ALLOWABLE DEGREE OF DANGEROUSNESS |
|---|---|---|
| LESS THAN 2000 | I | LESS THAN 1 cm |
| EQUAL TO OR MORE THAN 2000 AND LESS THAN 5000 | II | LESS THAN 3 cm |
| EQUAL TO OR MORE THAN 5000 | III | LESS THAN 10 cm |

214

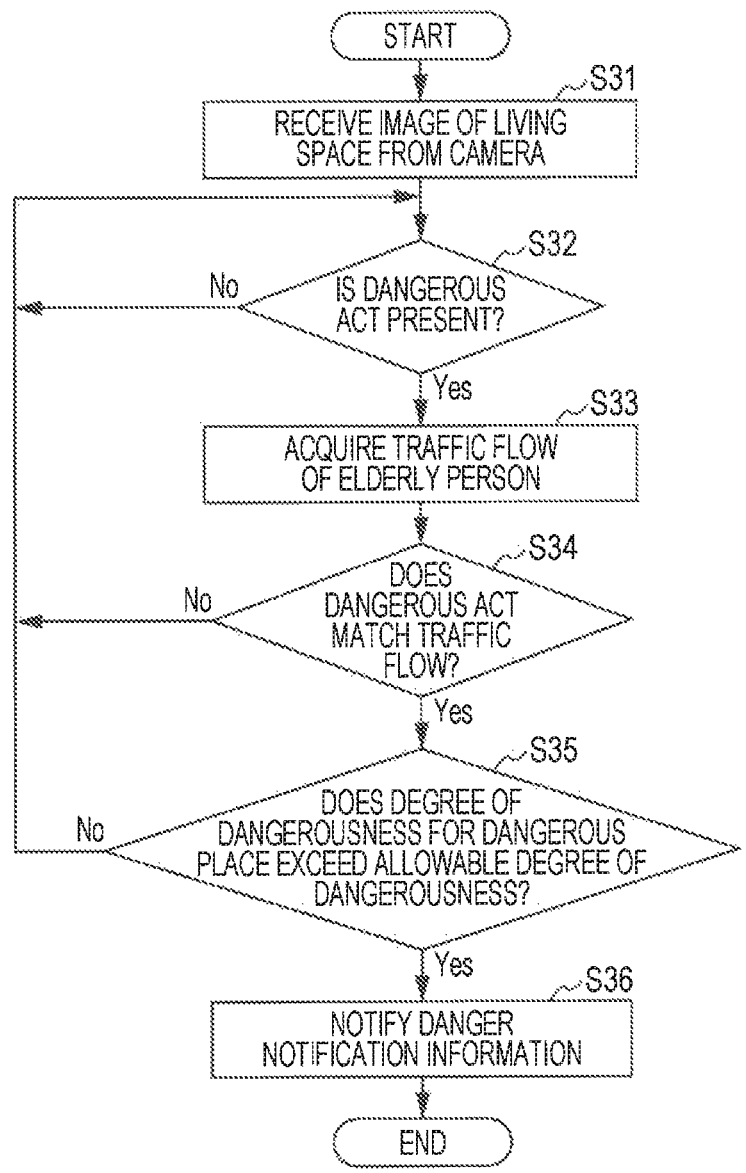

MONITORING APPARATUS FOR MONITORING A TARGETS EXPOSURE TO DANGER

CROSS-REFERENCE TO RELATED APPLICATIONS

This application is based on and claims priority under 35 USC 119 from Japanese Patent Application No. 2016-239762 filed Dec. 9, 2016.

BACKGROUND

Technical Field

The present invention relates to a monitoring apparatus and a non-transitory computer readable medium.

SUMMARY

According to an aspect of the invention, there is provided a monitoring apparatus including a detector and a notifying unit. The detector detects, based on an image obtained by capturing an image of a space in which a monitoring target acts, an act which is likely to cause the monitoring target to be exposed to danger. The notifying unit sends, in accordance with the act and an exercise ability of the monitoring target, a notification indicating that the monitoring target is likely to be exposed to danger.

BRIEF DESCRIPTION OF THE DRAWINGS

Exemplary embodiments of the present invention will be described in detail based on the following figures, wherein:

FIG. 3 is a diagram illustrating an example of dangerous place information;

FIG. 4 is a diagram illustrating an example of allowable degree of dangerousness information;

FIG. 12 is a flowchart illustrating an example of an operation of the monitoring server for monitoring an elderly person according to the third exemplary embodiment.

DETAILED DESCRIPTION

Figure 1:
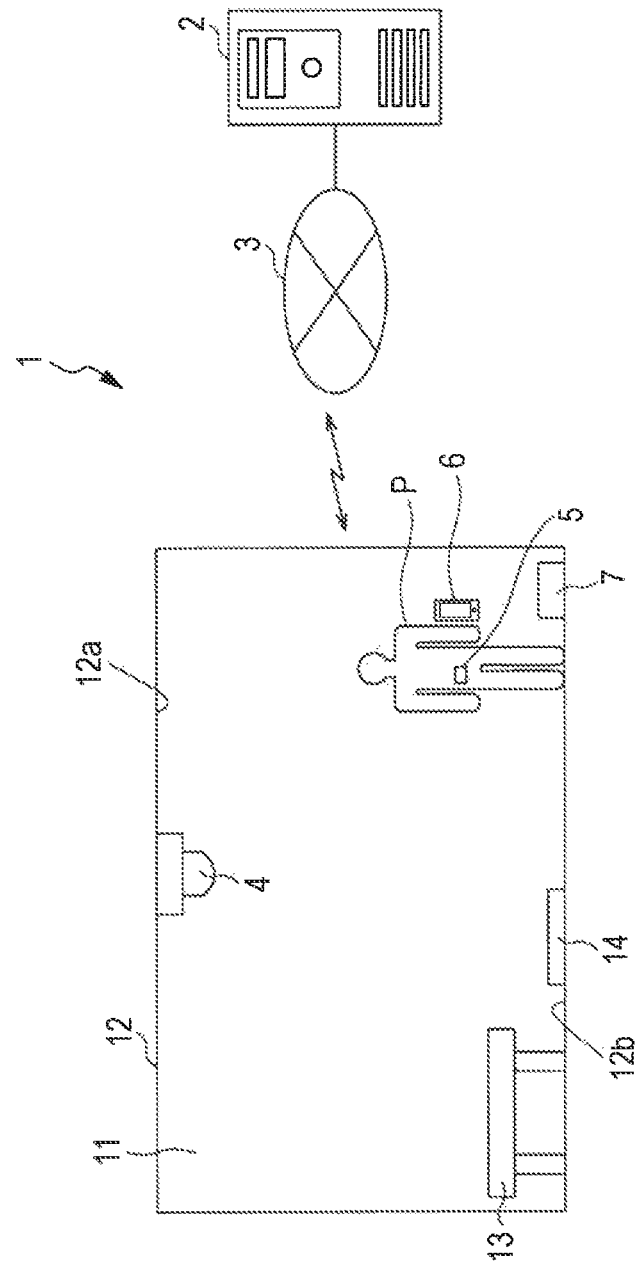
FIG. 1 is a diagram illustrating a schematic configuration example of a monitoring system according to a first exemplary embodiment of the present invention.

Exemplary embodiments of the present invention will be described below with reference to drawings. In individual drawings, components provided with substantially the same function will be referred to with the same reference sign, and redundant explanation will be omitted.

[Digest of Exemplary Embodiments]

A monitoring apparatus according to an exemplary embodiment includes a detector that detects, based on an image obtained by capturing an image of a space in which a monitoring target acts, an act which is likely to cause the monitoring target to be exposed to danger; and a notifying unit that sends, in accordance with the detected act and an exercise ability of the monitoring target, a notification indicating that the monitoring target is likely to be exposed to danger.

The monitoring target may be an elderly person or a person with a lower exercise ability than average. The space in which the target to be monitored (monitoring target) acts corresponds to a predetermined space inside, for example, a house, a nursing facility, a hospital, or a plant. Walking ability is an example of the exercise ability. However, the present invention is not limited to this. For example, muscular strength corresponding to a detected act may be defined as exercise ability.

The act which is likely to cause the monitoring target to be exposed to danger (hereinafter, may also be referred to as a "dangerous act") may be, for example, an act of the monitoring target of approaching a dangerous place (for example, within 10 cm), an act of the monitoring target of climbing upward (dangerous place), an act of placing an object as an obstacle or laying out a cable in a traffic flow of the monitoring target, or an act of climbing upward or walking while carrying a heavy baggage. The dangerous place represents a place where the monitoring target is likely to be exposed to danger, and may be, for example, a step or a cable. The traffic flow represents a path through which the monitoring target often passes. A path through which the monitoring target passes plural times (for example, twice) a day may be defined as a traffic flow.

For example, the detector may extract an object such as a human being or a subject from a captured image and detect a dangerous act by performing pattern matching or the like with a reference object as a dangerous act. The image may be a still image or a moving image. The detector detects, based on motion of the object extracted from the image, a dangerous act. It is desirable to learn in advance, through machine learning such as Deep Learning, which act is defined as a dangerous act.

The notifying unit may send a notification by indicating an image or producing sound. The notifying unit may send a notification to a portable device carried by the monitoring target or the monitoring apparatus itself may send a notification.

The detector detects, based on the image obtained by capturing an image of the space in which the monitoring target acts, an act which is likely to cause the monitoring target to be exposed to danger. The notifying unit sends, in accordance with the act detected by the detector and an exercise ability of the monitoring target, a notification indicating that the monitoring target is likely to be exposed to danger.

First Exemplary Embodiment

FIG. 1 is a diagram illustrating a schematic configuration example of a monitoring system according to a first exemplary embodiment of the present invention. A monitoring system 1 includes a monitoring server 2 which monitors an elderly person P who acts in a living space 11 inside a house 12, a camera 4 provided at a ceiling 12a of the house 12, a wearable device 5 mounted on the elderly person P, a portable device 6 carried by the elderly person P, and a robot 7 which travels on a floor surface 12b of the house 12. The living space 11 is an example of a space. The elderly person P is an example of a monitoring target.

The camera 4, the wearable device 5, the portable device 6, and the robot 7 are connected to the monitoring server 2 via a network 3 such as the Internet. The camera 4, the wearable device 5, the portable device 6, and the robot 7 each include a radio communication function such as Wi-Fi, and perform transmission and reception of information to and from the monitoring server 2 via the network 3.

In the first exemplary embodiment, on the floor surface 12b of the house 12, furniture such as a desk 13 is placed and a step 14 is provided.

When it is determined that the elderly person P is likely to be exposed to danger, the monitoring server 2 sends the portable device 6 carried by the elderly person P a push notification, for example, a warning indicating that the elderly person P is likely to be exposed to danger.

The camera 4 captures, for example, still images. The camera 4 transmits to the monitoring server 2 still images obtained by periodically (for example, every few seconds) capturing an image of the living space 11, along with a building ID for identifying the house 12. The camera 4 is an example of an image capturing device. The image capturing device may be a video camera which captures moving images as long as it may continuously capture images. Furthermore, capturing of still images or moving images may be started when the elderly person P starts moving, and capturing of still images or moving images may be stopped when moving is stopped for a certain period of time.

The wearable device 5 is provided with a function of measuring the daily number of steps, and periodically (for example, every day or every week) transmits measured data of the daily number of steps, along with a target ID for identifying the elderly person P, to the monitoring server 2. The data of the daily number of steps is an example of information of walking ability. The information of walking ability is not necessarily the daily number of steps. The information of walking ability may be, for example, walking speed. The wearable device 5 is mounted on a waist, head, arm, or the like, and may be of a belt type, a glasses type, an earphone type, a wrist type, or the like.

The portable device 6 indicates the layout of the living space 11, and indicates, in an emphasized manner, a dangerous place which is determined to be likely to cause the elderly person P to be exposed to danger. The portable device 6 may be, for example, a multifunction telephone such as a smartphone.

The robot 7 is an automatic travelling robot which autonomously travels based on simultaneous localization and mapping (SLAM) technology. The SLAM technology is known as a technology in which a mobile body such as an autonomous travel robot estimates its own location and creates environmental map data at the same time while autonomously moving. The environmental map data includes three-dimensional positional information of various materials (in FIG. 1, the desk 13, the step 14, etc.) installed in an environment (in FIG. 1, the living space) in which the robot 7 travels. Upon creating environmental map data, the robot 7 transmits the created environmental map data along with a building ID to the monitoring server 2 via the network 3. The robot 7 is an example of a mobile body.

Figure 2:
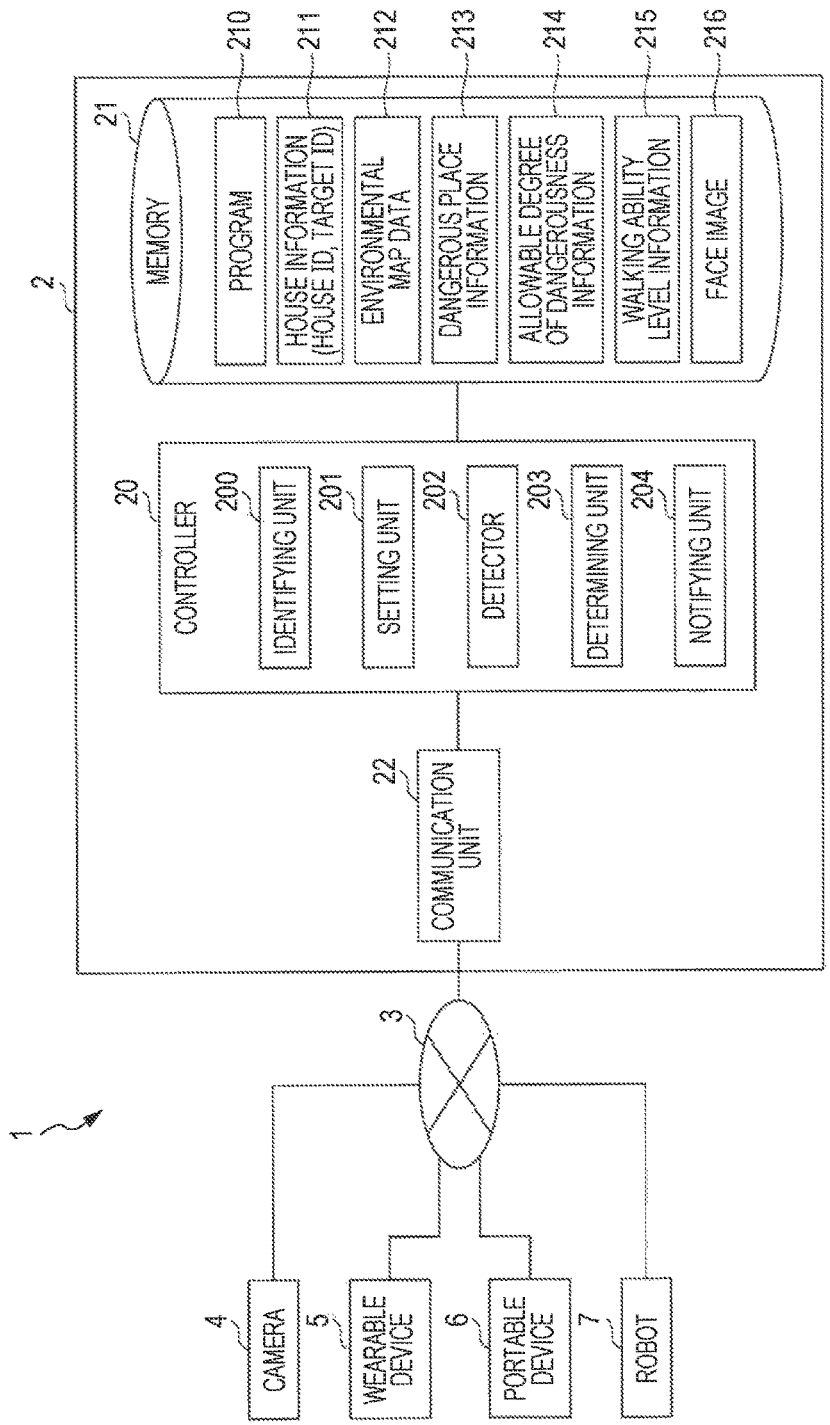
FIG. 2 is a block diagram illustrating an example of a control system of the monitoring system according to the first exemplary embodiment.

FIG. 2 is a block diagram illustrating an example of a control system of the monitoring system 1 according to the first exemplary embodiment.

The monitoring server 2 includes a controller 20 which controls each unit of the monitoring server 2, a memory 21 which stores various types of information, and a communication unit 22 which is connected to the network 3.

The camera 4, the wearable device 5, the portable device 6, and the robot 7 are connected to the monitoring server 2 via the network 3, as described above.

The controller 20 includes a central processing unit (CPU), an interface, and so on. The controller 20 functions as an identifying unit 200, a setting unit 201, a detector 202, a determining unit 203, a notifying unit 204, and the like by operating in accordance with a program 210. Details of each of the identifying unit 200, the setting unit 201, the detector 202, the determining unit 203, and the notifying unit 204 will be described later. The setting unit 201 is an example of an acquisition unit.

The memory 21 includes a read only memory (ROM), a random access memory (RAM), a hard disk, and the like, and stores various types of data including the program 210, house information 211, environmental map data 212, dangerous place information 213, allowable degree of dangerousness information 214, walking ability level information 215, and a face image 216.

The house information 211 includes a building ID for identifying the house 12 and a target ID for identifying the elderly person P who acts in the living space 11 of the house 12. In the first exemplary embodiment, only one elderly person P is present. However, plural elderly people P may act in the living space 11 of the same house 12. In the case where plural elderly people P are present, one camera 4 and one robot 7 are arranged in one house 12, whereas each elderly person P owns the wearable device 5 and the portable device 6. Plural cameras 4 may be provided to eliminate blind spots. Furthermore, one house 12 may include plural living spaces 11.

Data of the daily number of steps for, for example, one month is stored in the walking ability level information 215. In addition to data of the number of steps, walking ability level is also registered in the walking ability level information 215.

The face image 216 is stored in the memory 21 in association with a target ID.

The identifying unit 200 identifies a dangerous place inside the living space 11 and the degree of dangerousness representing the degree of dangerousness at the dangerous place. That is, the identifying unit 200 acquires the environmental map data 212 from the memory 21, and identifies in advance, based on the environmental map data 212, the location of a dangerous place, a dangerous target (type of dangerous place), and the degree of dangerousness. The identifying unit 200 stores, as the dangerous place information 213, the identified location of the identified dangerous place, the dangerous target, and the degree of dangerousness in association with a building ID in the memory 21. The degree of dangerousness is represented by, for example, height.

The setting unit 201 sets, based on the average daily number of steps of the elderly person P, the allowable degree of dangerousness representing the possibility that the elderly person P may be exposed to danger. That is, the possibility that danger may be present may be high or low, and the possibility of danger is determined based on the allowable degree of dangerousness. The setting unit 201 acquires data of the daily number of steps of the elderly person P periodically transmitted from the wearable device 5 to the monitoring server 2, and stores the acquired data in the allowable degree of dangerousness information 214 of the memory 21. The setting unit 201 calculates the average daily number of steps of the elderly person P based on the allowable degree of dangerousness information 214, sets the walking ability level in accordance with the calculated average daily number of steps, and stores the walking ability level in the walking ability level information 215 in the memory 21. The average daily number of steps is an example of information of walking ability.

The detector 202 detects the current location based on an image obtained by capturing an image of the living space 11 in which the elderly person P acts and environmental map data, and detects an act of the elderly person P of approaching a dangerous place. At this time, the detector 202 extracts a face image from the image, and collates the extracted face image with the face image 216 which is registered in advance. In the case where the extracted face image matches the registered face image 216, the detector 202 detects the current location of the elderly person P. The camera 4 captures an image including a peripheral region of the elderly person P. The detector 202 collates the peripheral region of the elderly person P with the environmental map data 212, acquires the location of the peripheral region from the environmental map data 212, and detects, based on the location of the peripheral region, the current location of the elderly person P. When the distance between the current location of the elderly person P and the dangerous place is equal to or less than a predetermined distance, the detector 202 detects that the elderly person P has approached the dangerous place. The detector 202 notifies the determining unit 203 of the dangerous place that the elderly person P has approached.

The determining unit 203 determines, based on the dangerous place notified from the detector 202 and walking ability level, whether or not the possibility that the elderly person P may be exposed to danger is high. That is, when the elderly person P has approached a dangerous place, in a case where the degree of dangerousness for the dangerous place exceeds the allowable degree of dangerousness for the elderly person P, the determining unit 203 determines that the possibility that the elderly person P may be exposed to danger is high. When the elderly person P has approached a dangerous place, in the case where the degree of dangerousness for the dangerous place is less than or equal to the allowable degree of dangerousness for the elderly person P, the determining unit 203 determines that the possibility that the elderly person P may be exposed to danger is low.

The notifying unit 204 sends, in accordance with the dangerous place detected by the detector 202 and the walking ability level of the elderly person P, a notification indicating that the elderly person P is likely to be exposed to danger. That is, in the case where the determining unit 203 determines that the possibility that the elderly person P may be exposed to danger is high, the notifying unit 204 notifies the portable device 6 of danger notification information. The danger notification information is an example of information indicating that danger may be present.

The danger notification information includes the layout of the living space 11 and a dangerous place which is determined to be highly likely to cause the elderly person P to be exposed to danger. The dangerous place is indicated in an emphasized manner such that the dangerous place is more noticeable than around the dangerous place. Emphasized indication may be indicating a dangerous place in a noticeable color such as red, indicating the dangerous place in a blinking manner, or indicating the dangerous place in a circle.

(Operation of First Exemplary Embodiment)

Next, an example of an operation of the monitoring system 1 according to the first exemplary embodiment will be described with reference to FIGS. 3 to 6.

(1) Identify Dangerous Place and Degree of Dangerousness

The robot 7 creates environmental map data by traveling on the floor surface 12*b* of the house 12. The robot 7 transmits the created environmental map data along with a building ID to the monitoring server 2 via the network 3. The controller 20 of the monitoring server 2 stores, in association with the building ID, the environmental map data 212 transmitted from the robot 7 in the memory 21.

The identifying unit 200 reads the environmental map data 212 from the memory 21, and identifies, based on the environmental map data 212, a dangerous place and the degree of dangerousness. The identifying unit 200 stores, as the dangerous place information 213, the identified dangerous place and degree of dangerousness in association with the building ID in the memory 21.

FIG. 3 is a diagram illustrating an example of the dangerous place information 213. The dangerous place information 213 includes, for example, the location (point or plane) of a dangerous place, the degree of dangerousness, and a dangerous target (may be called an object). For example, the location of a dangerous place is represented by coordinates (longitude and latitude) at a point for a narrow region and is represented by a plane (for example, a rectangular plane formed by connecting four coordinates by straight lines) for a wide region. The degree of dangerousness is represented by, for example, the height from the floor surface 12*b*. The dangerous target is represented by, for example, a step or a cable of 1 meter long. For example, an object is easily caught in a cable compared to a step with the same height. Therefore, the degree of dangerousness may depend on the dangerous target (type of dangerous place). The identifying unit 200 may register the dangerous place information 213 in the environmental map data 212. Furthermore, the identifying unit 200 may analyze big data of a past accident case, extract an object which caused the accident, and register the extracted object in the environmental map data 212.

(2) Setting of Walking Ability Level

Figure 5:
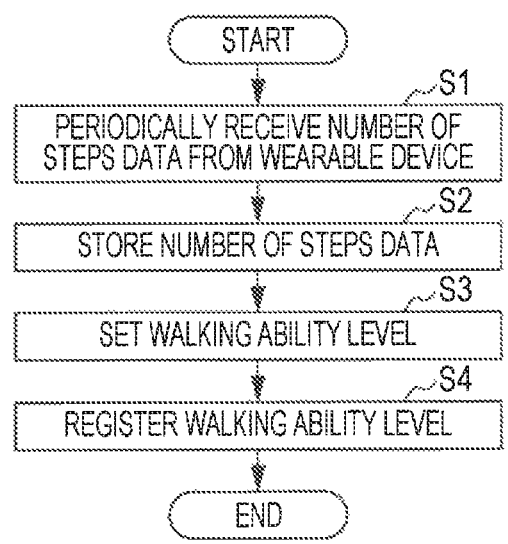
FIG. 5 is a flowchart illustrating an example of an operation of a monitoring server for setting a walking ability level according to the first exemplary embodiment.

FIG. 5 is a flowchart illustrating an example of an operation of the monitoring server 2 for setting walking ability level. The wearable device 5 periodically transmits data of the daily number of steps along with a target ID to the monitoring server 2 via the network 3. The monitoring server 2 periodically receives data of the daily number of steps from the wearable device 5 (S1). The controller 20 of the monitoring server 2 stores the received data of the daily number of steps in association with the target ID in the walking ability level information 215 in the memory 21 (S2). For example, when data of the number of steps for one month is stored in the walking ability level information 215, the setting unit 201 calculates the average daily number of steps, and sets the walking ability level of the elderly person P corresponding to the average daily number of steps by referring to the allowable degree of dangerousness information 214 (S3).

FIG. 4 is a diagram illustrating an example of the allowable degree of dangerousness information 214. The allowable degree of dangerousness information 214 includes an average daily number of steps field in which the average daily number of steps is recorded, a walking ability level field in which walking ability level is recorded, and an allowable degree of dangerousness field in which the allowable degree of dangerousness is recorded. For example, in the case where the average daily number of steps of the elderly person P is 3000 steps/day, the setting unit 201 sets walking ability level II, and registers the walking ability level II in association with a target ID in the walking ability level information 215 in the memory 21 (S4).

(2) Monitoring

Figure 6:
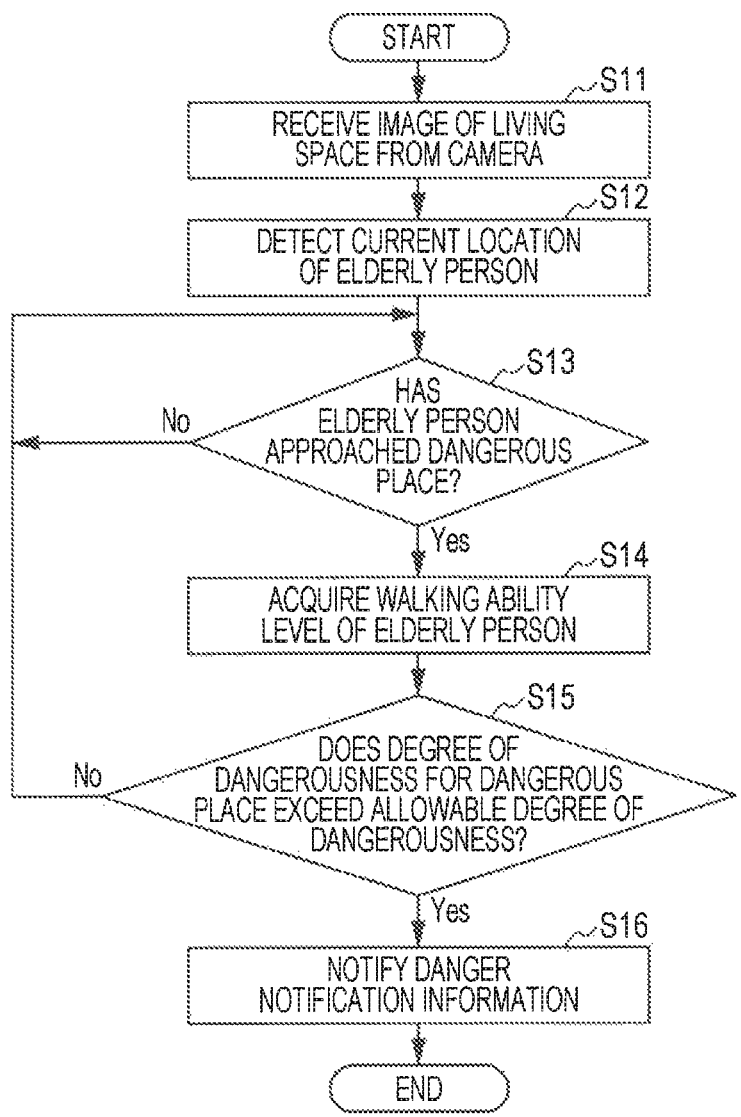
FIG. 6 is a flowchart illustrating an example of an operation of the monitoring server for monitoring an elderly person according to the first exemplary embodiment.

FIG. 6 is a flowchart illustrating an example of an operation of the monitoring server 2 for monitoring the elderly person P. The monitoring server 2 periodically receives captured images of the living space 11 from the camera 4 (S11).

The detector 202 extracts a face image from an image transmitted from the camera 4, and collates the extracted face image with the face image 216 registered in advance. In the case where the extracted face image matches the registered face image 216, the detector 202 detects the current location of the elderly person P from the image.

The detector 202 collates a peripheral region of the elderly person P in the image captured by the camera 4 with the environmental map data 212, and detects, based on the location of the peripheral region, the current location of the elderly person P.

In the case where the distance between the current location of the elderly person P and a dangerous place is less than or equal to a predetermined distance, the detector 202 detects that the elderly person P has approached the dangerous place (S13: Yes). The detector 202 notifies the determining unit 203 of the dangerous place that the elderly person P has approached.

The determining unit 203 acquires, based on the walking ability level information 215 in the memory 21, the walking ability level of the elderly person P (S14). In the case where the average daily number of steps of the elderly person P is 3000 steps/day, the determining unit 203 acquires the walking ability level II.

The determining unit 203 determines whether or not the degree of dangerousness for the dangerous place exceeds the walking ability of the elderly person P (S15). The determining unit 203 acquires, based on the allowable degree of dangerousness information 214, the allowable degree of dangerousness corresponding to the walking ability level II (less than 3 cm). The determining unit 203 acquires, based on positional information of the dangerous place, the degree of dangerousness by referring to the dangerous place information 213. In the case where the location of the dangerous place is represented by (x1, y1), the degree of dangerousness (4 cm) is acquired. In this case, the acquired degree of dangerousness (4 cm) is more than the allowable degree of dangerousness (less than 3 cm). Therefore, the determining unit 203 determines that the possibility that the elderly person P may be exposed to danger is high (S15: Yes).

The notifying unit 204 notifies the portable device 6 of danger notification information, the portable device 6 being carried by the elderly person P who is determined to be highly likely to be exposed to danger (S16).

Based on the danger notification information, the portable device 6 indicates the layout of the living space 11, and indicates, in an emphasized manner, a dangerous place which is determined to be highly likely to cause the elderly person P to be exposed to danger. The elderly person P avoids the dangerous place (for example, a step) indicated on the portable device 6 or walks carefully.

Second Exemplary Embodiment

Figure 7:
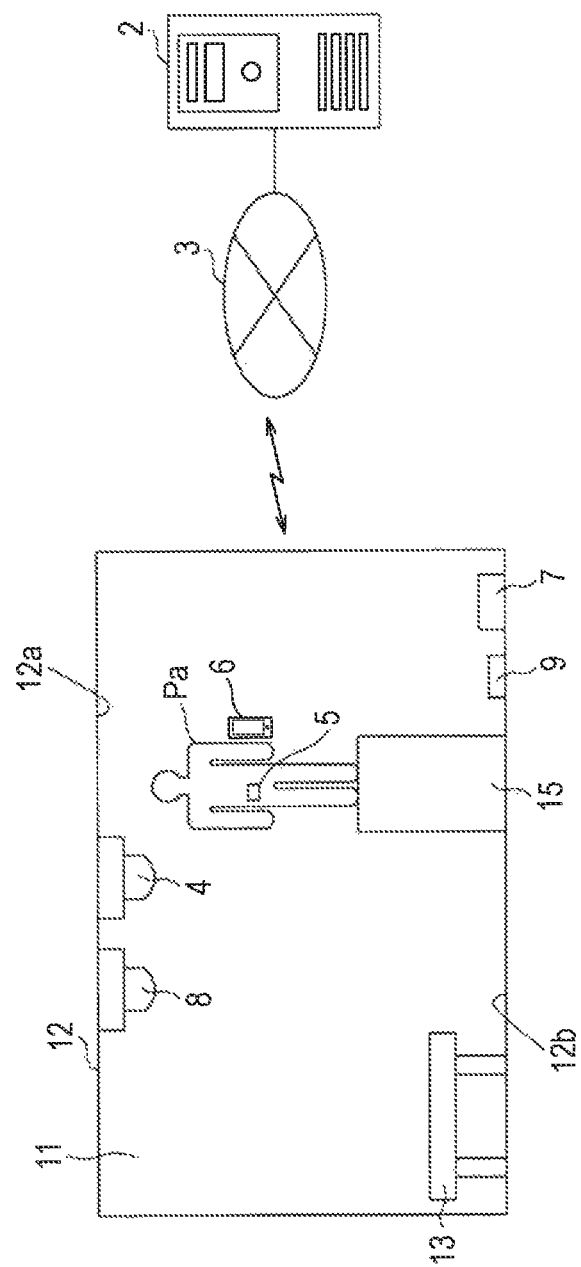
FIG. 7 is a diagram illustrating a schematic configuration example of a monitoring system according to a second exemplary embodiment of the present invention.

FIG. 7 is a diagram illustrating a schematic configuration example of a monitoring system according to a second exemplary embodiment of the present invention. In the first exemplary embodiment, an act of the elderly person P of approaching a dangerous place has been explained as a danger act. However, in the second exemplary embodiment, an act of the elderly person P of climbing an upper dangerous place will be explained. Differences from the first exemplary embodiment will be focused on below.

The monitoring system 1 includes, as in the first exemplary embodiment, the camera 4, a wearable device 5a, the portable device 6, the robot 7, and the monitoring server 2. The monitoring system 1 further includes a PATLITE® 8 which is provided at the ceiling 12a of the house 12.

The camera 4, the wearable device 5a, the portable device 6, the robot 7, and the PATLITE 8 each include a radio communication function such as Wi-Fi, and perform transmission and reception of information to and from the monitoring server 2 via the network 3.

In the second exemplary embodiment, furniture such as the desk 13 and a stepladder 15 are arranged on the floor surface 12b of the house 12.

The wearable device 5a is different from the first exemplary embodiment in that the wearable device 5a includes a barometer. The wearable device 5a acquires an atmospheric pressure value from an external barometer 9 arranged on the floor surface 12b, acquires information of the height of the wearable device 5a from the floor surface 12b, based on a difference between the acquired atmospheric pressure value and a measured value of the barometer of the wearable device 5a, and transmits the information of the height to the monitoring server 2.

When a driving signal is transmitted, the PATLITE 8 rotates a light projector and produces alarm sound.

Figure 8:
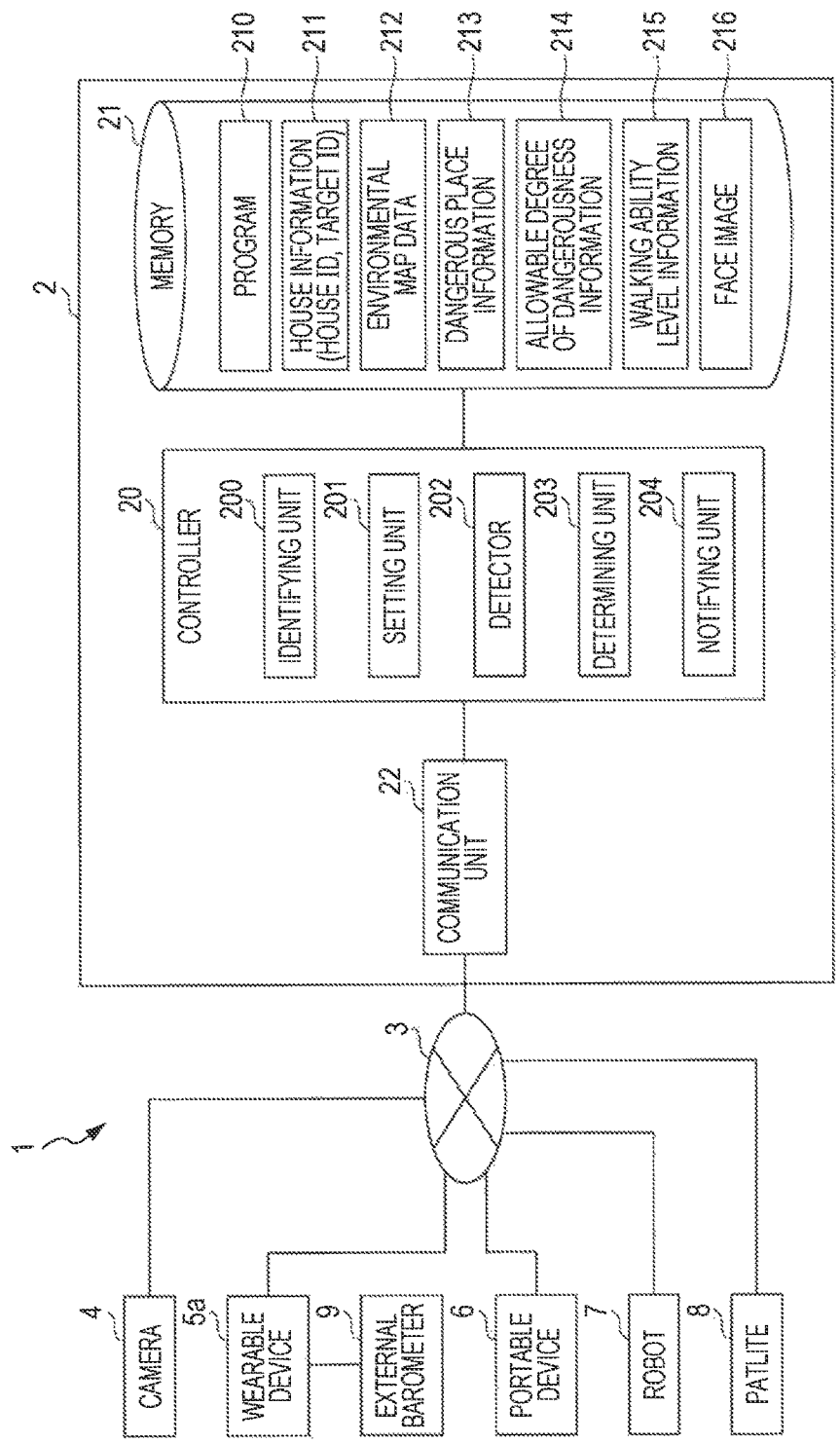
FIG. 8 is a block diagram illustrating an example of a control system of the monitoring system according to the second exemplary embodiment.

FIG. 8 is a block diagram illustrating an example of a control system of the monitoring system 1 according to the second exemplary embodiment. The monitoring system 1 according to the second exemplary embodiment includes, as in the first exemplary embodiment, the camera 4, the wearable device 5a, the portable device 6, and the robot 7, which are connected to the monitoring server 2 via the network 3, and the PATLITE 8 is also connected to the monitoring server 2 via the network 3.

The monitoring server 2 includes, as in the first exemplary embodiment, the controller 20, the memory 21, and the communication unit 22.

In the memory 21, as in the first exemplary embodiment, the program 210, the house information 211, the environmental map data 212, the dangerous place information 213, the allowable degree of dangerousness information 214, the walking ability level information 215, the face image 216, and the like are stored.

The allowable degree of dangerousness information 214 stored in the memory 21 includes, as in the first exemplary embodiment, the average daily number of steps field, the walking ability level field, and the allowable degree of dangerousness field. However, in the second exemplary embodiment, as the allowable degree of dangerousness, the height to which climbing is allowed is recorded in the allowable degree of dangerousness field.

The controller 20 functions as the identifying unit 200, the setting unit 201, the detector 202, the determining unit 203, the notifying unit 204, and the like by operating in accordance with the program 210, as in the first exemplary embodiment.

The detector 202 detects, as a dangerous act, an act of the elderly person P of climbing to an upper dangerous place. That is, the detector 202 acquires information of height of the elderly person P from the wearable device 5a, and when the acquired height exceeds a predetermined height, the detector 202 may detect an act of the elderly person P of climbing an upper dangerous place as a dangerous act. The detector 202 notifies the determining unit 203 of the height acquired from the wearable device 5a.

When the detector 202 detects an act of climbing an upper dangerous place, the determining unit 203 acquires, based on the walking ability level information 215, the walking ability level of the elderly person P, and acquires, based on the allowable degree of dangerousness information 214, the walking ability level and the height as the allowable degree of dangerousness. Then, in the case where the height of the upper dangerous place as the degree of dangerousness exceeds the height as the allowable degree of dangerousness, the determining unit 203 determines that the possibility that the elderly person P may be exposed to danger is high.

In the case where the determining unit 203 determines that the possibility that the elderly person P may be exposed to danger is high, the notifying unit 204 transmits a driving signal for driving the PATLITE 8 to the PATLITE 8. The PATLITE 8 rotates the light projector based on the transmitted driving signal, and produces alarm sound. The PATLITE 8 is attached to the ceiling 12a, and therefore, the elderly person P who climbs upward easily notices the alarm. The elderly person P stops climbing upward or climbs carefully.

The notifying unit 204 may transmit danger notification information to the portable device 6, as in the first exemplary embodiment. The portable device 6 indicates danger notification information. The danger notification information includes the layout of the living space 11 and the stepladder 15 which relates to the dangerous act. The stepladder 15 may be indicated in an emphasized manner in the layout.

Third Exemplary Embodiment

Figure 9:
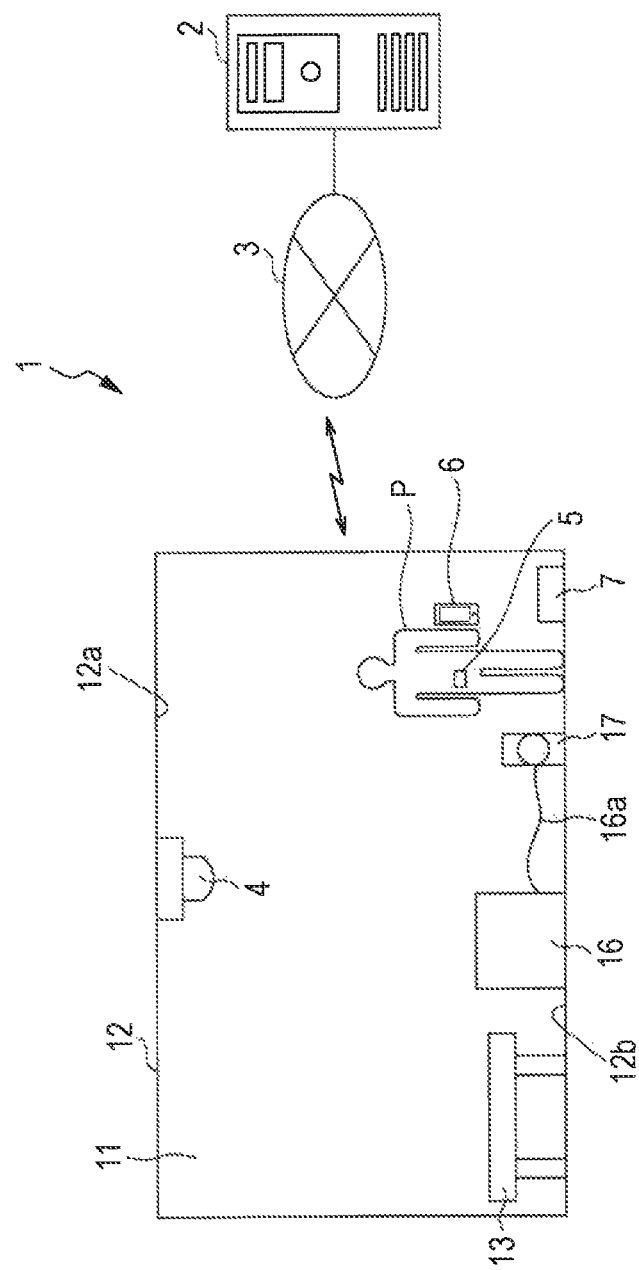
FIG. 9 is a diagram illustrating a schematic configuration example of a monitoring system according to a third exemplary embodiment of the present invention.

FIG. 9 is a diagram illustrating a schematic configuration example of a monitoring system according to a third exemplary embodiment of the present invention. In the first exemplary embodiment, an act of the elderly person P of approaching a dangerous place has been explained as a dangerous act. However, in the third exemplary embodiment, an act of placing an obstacle in a traffic flow of the elderly person P will be explained. Differences from the first exemplary embodiment will be focused on below.

The monitoring system 1 includes, as in the first exemplary embodiment, the monitoring server 2, the camera 4, the wearable device 5, the portable device 6, and the robot 7.

In the third exemplary embodiment, furniture such as the desk 13 and an electrical product such as an electric heater 16 are arranged on the floor surface 12b of the house 12. A cable 16a extending from the electric heater 16 is plugged into an outlet 17.

The camera 4 may compress periodically captured images of the living space 11 and transmit the compressed images to the monitoring server 2. For example, to reduce the amount of data transfer, a difference between the last captured image and the currently captured image is obtained, and an image of the difference is transmitted to the monitoring server 2. In the case where the elderly person P is not active, the amount of data transfer is extremely small.

Figure 10:
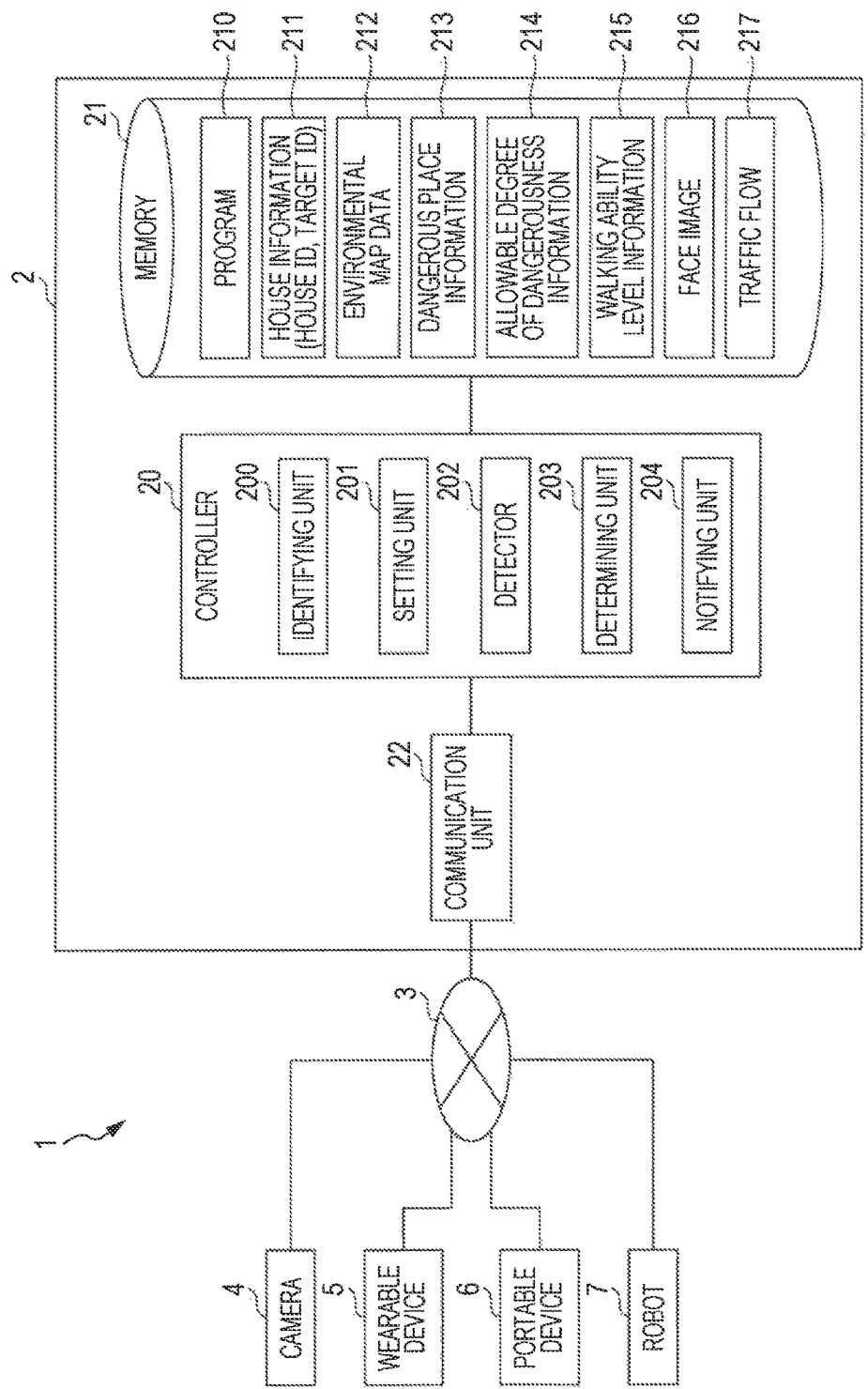
FIG. 10 is a block diagram illustrating an example of a control system of the monitoring system according to the third exemplary embodiment.

FIG. 10 is a block diagram illustrating an example of a control system of the monitoring system 1 according to the third exemplary embodiment. The monitoring system 1 according to the third exemplary embodiment includes, as in the first exemplary embodiment, the camera 4, the wearable device 5, the portable device 6, and the robot 7, which are connected to the monitoring server 2 via the network 3.

The monitoring server 2 includes, as in the first exemplary embodiment, the controller 20, the memory 21, and the communication unit 22.

In the memory 21, as in the first exemplary embodiment, the program 210, the house information 211, the environmental map data 212, the dangerous place information 213, the allowable degree of dangerousness information 214, the walking ability level information 215, the face image 216, and the like are stored. In addition to the above, a traffic flow 217 is also stored in the memory 21.

The allowable degree of dangerousness information 214 stored in the memory 21 includes, as in the first exemplary embodiment, the average daily number of steps field, the walking ability level field, and the allowable degree of dangerousness field. However, in the third exemplary embodiment, in the allowable degree of dangerousness field, an allowable degree of dangerousness for a dangerous place appearing in a traffic flow, such as height (including zero), is registered as the allowable degree of dangerousness.

The controller 20 functions as the identifying unit 200, the setting unit 201, the detector 202, the determining unit 203, the notifying unit 204, and the like by operating in accordance with the program 210, as in the first exemplary embodiment.

The detector 202 detects the traffic flow 217 of the elderly person P in accordance with changes in the current location of the elderly person P, and stores the detected traffic flow 217 in the memory 21. Furthermore, the detector 202 detects a dangerous place appearing in the living space 11 in accordance with changes in a captured image, and identifies the degree of dangerousness for the dangerous place. For example, in the case where an object, such as the cable 16a, which was not present in the image, appears in the image, the detector 202 detects the height of the cable 16a, detects the cable 16a as a dangerous place, and detects an act of laying out the cable 16a as a dangerous act. The detector 202 may, for example, detect an act of an object in accordance with inter-frame prediction and motion compensation of compression data.

When a dangerous place with a degree of dangerousness exceeding the allowable degree of dangerousness appears in a traffic flow, the determining unit 203 determines that the possibility that the elderly person P may be exposed to danger is high.

Operation of Third Exemplary Embodiment

Next, an example of an operation of the monitoring system 1 according to the third exemplary embodiment will be described with reference to FIGS. 11 and 12.

(1) Recording of Traffic Flow

Figure 11:
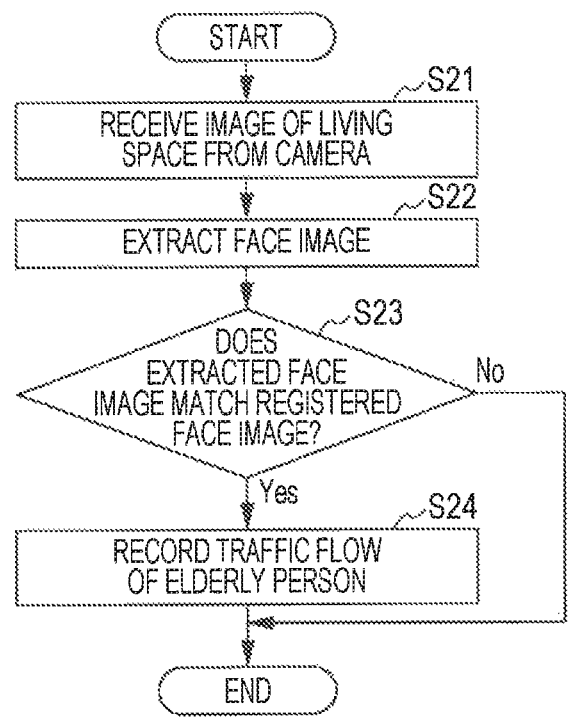
FIG. 11 is a flowchart illustrating an example of an operation of the monitoring server for recording a traffic flow according to the third exemplary embodiment.

FIG. 11 is a flowchart illustrating an example of an operation of the monitoring server 2 for recording a traffic flow. The monitoring server 2 periodically receives captured images of the living space 11 from the camera 4 (S21).

The detector 202 extracts a face image from an image transmitted from the camera 4 (S22), collates the extracted face image with the face image 216 registered in advance, and determines whether or not the extracted face image matches the registered face image 216 (S23). In the case where the extracted face image matches the registered reface image 216 (S23: Yes), the detector 202 detects the current location of the elderly person P, detects a moving path of the elderly person P by continuously performing the above processing, and records the moving path as the traffic flow 217 in the memory 21 (S24). In the case where the extracted face image does not match the registered face image 216 (S23: No), a moving path is not detected, and the traffic flow 217 is not recorded, because the target is not the registered elderly person P.

(2) Monitoring

FIG. 12 is a flowchart illustrating an example of an operation of the monitoring server 2 for monitoring the elderly person P. The monitoring server 2 periodically receives captured images of the living space 11 from the camera 4 (S31).

The detector 202 determines whether or not a dangerous act is present (S32). For example, a third party plugs the cable 16a of the electric heater 16 into the outlet 17. In the case where the cable 16a, which was not present in the image, appears in the image, the cable 16a is detected as a dangerous act, and the height of the cable 16a is detected (S32: Yes).

The determining unit 203 acquires the traffic flow 217 of the elderly person P from the memory 21, and determines whether or not a place where a danger act is being performed matches the traffic flow 217 (S34).

In the case where the dangerous place where the danger act is being performed matches the traffic flow 217 (S34: Yes) and the degree of dangerousness for the dangerous place exceeds the allowable degree of dangerousness (S35), the determining unit 203 determines that the possibility that the elderly person P may be exposed to danger is high.

The notifying unit 204 transmits danger notification information to the portable device 6 carried by the elderly person P who is determined to be highly likely to be exposed to danger.

The portable device 6 indicates the layout of the living space 11 based on danger notification information, and indicates, in an emphasized manner, an act which is determined to be highly likely to cause the elderly person P to be exposed to danger. The elderly person P causes the dangerous act indicated on the portable device 6, such as connection of the cable 16a, to be stopped or causes the dangerous act to be performed such that a traffic flow is avoided.

The exemplary embodiments of the present invention have been described above. However, the exemplary embodiments of the present invention are not limited to the foregoing exemplary embodiments. Various modifications and embodiments are possible without departing from the gist of the present invention.

Each unit of the controller 20 may be partly or entirely configured by a hardware circuit such as a field programmable gate array (FPGA) or an application specific integrated circuit (ASIC).

Furthermore, part of components of the foregoing exemplary embodiments may be omitted or changed without departing from the gist of the present invention. Furthermore, addition, deletion, change, replacement, or the like of steps is possible in a flow of the foregoing exemplary embodiments without departing from the gist of the present invention. Furthermore, a program used in the foregoing exemplary embodiments may be recorded in a computer-readable recording medium such as a compact disc-read only memory (CD-ROM) and supplied or the program may be stored in an external server such as a cloud server and used via a network.

The foregoing description of the exemplary embodiments of the present invention has been provided for the purposes of illustration and description. It is not intended to be exhaustive or to limit the invention to the precise forms disclosed. Obviously, many modifications and variations will be apparent to practitioners skilled in the art. The embodiments were chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

What is claimed is:

1. A monitoring apparatus comprising:
    a detector, implemented on one or more processors, that receives an image from an image capturing device, the image being of an environment in which a monitoring target acts, and determines whether an act captured in the image is likely to cause the monitoring target to be exposed to danger, the act including the monitoring target moving towards a preselected location within a preselected range of an object in the environment; and
    a notifying unit, implemented on the one or more processors, that sends over a network, in accordance with a determination that the act is likely to expose the monitoring target to harm based on the act and a predetermined fitness level of the monitoring target, a notification indicating that the monitoring target is likely to be exposed to danger to at least one of the monitoring target and a third party.

2. The monitoring apparatus according to claim 1, further comprising:
    an identifying unit, implemented on the one or more processors, that identifies a dangerous place in the environment and a degree of dangerousness indicating a degree of dangerousness at the dangerous place, the dangerous place being a location within range of another object in the environment; and
    a setting unit, implemented on the one or more processors, that sets, based on information of the predetermined fitness level, an allowable degree of dangerousness indicating a possibility that the monitoring target may be exposed to danger,
    wherein when the monitoring target approaches the dangerous place with a degree of dangerousness exceeding the allowable degree of dangerousness, the notifying unit sends a notification indicating that the monitoring target is likely to be exposed to danger.

3. The monitoring apparatus according to claim 2,
    wherein the identifying unit acquires environmental map data of the environment and identifies, based on the environmental map data, the dangerous place and the degree of dangerousness, and
    wherein the detector detects, based on the environmental map data and the image, the act of approaching the dangerous place.

4. The monitoring apparatus according to claim 1, further comprising:
an identifying unit, implemented on the one or more processors, that identifies a dangerous place in the environment and a degree of dangerousness indicating a degree of dangerousness at the dangerous place, the dangerous place being a location within range of another object in the environment; and
a setting unit, implemented on the one or more processors, that sets, based on information of the predetermined fitness level, an allowable degree of dangerousness indicating a possibility that the monitoring target may be exposed to danger,
wherein the detector detects the monitoring target climbing an upper dangerous place, and
wherein when the monitoring target climbs toward the dangerous place with a degree of dangerousness exceeding the allowable degree of dangerousness, and the notifying unit sends a notification indicating that the monitoring target is likely to be exposed to danger.

5. The monitoring apparatus according to claim 1, further comprising:
an identifying unit, implemented on the one or more processors, that identifies, based on a change in the image, a dangerous place appearing in the environment and a degree of dangerousness indicating a degree of dangerousness at the dangerous place; and
a setting unit, implemented on the one or more processors, that sets, based on information of the predetermined fitness level, an allowable degree of dangerousness indicating a possibility that the monitoring target may be exposed to danger,
wherein the detector detects, based on a change in a current location of the monitoring target, a traffic flow of the monitoring target, and detects, based on a change in the image, the dangerous place appearing in the environment, and
wherein the notifying unit sends, when the dangerous place with a degree of dangerousness exceeding the allowable degree of dangerousness appears in the traffic flow, a notification indicating that the monitoring target is likely to be exposed to danger.

6. The monitoring apparatus according to claim 1, wherein the fitness level is set based on a walking ability of the monitoring target.

7. The monitoring apparatus according to claim 1, wherein the fitness level is set based on a walking ability level of the monitoring target.

8. The monitoring apparatus according to claim 1, wherein the preselected range correlates to the predetermined fitness level of the monitoring target such that the greater the predetermined fitness level of the monitoring target, the shorter the preselected range is in determining whether the act captured in the image is likely to cause the monitoring target to be exposed to danger.

9. The monitoring apparatus according to claim 1, wherein
the detector further determines a moving path of the monitoring target,
the determination that the act is likely to expose the monitoring target to harm is further based on whether the moving path matches the act, and
the preselected range correlates to the predetermined fitness level of the monitoring target such that the greater the predetermined fitness level of the monitoring target, the shorter the preselected range is in determining whether the act, matching the moving path, is likely to cause the monitoring target to be exposed to danger, and
the predetermined fitness level is one of a plurality of predetermined fitness levels that each fall within a distinct range of a measurable criteria, and the predetermined fitness level is determined based on the measurable criteria obtained for the monitoring target.

10. A non-transitory computer readable medium storing a program causing a computer to execute a process for monitoring, the process comprising:
detecting, based on an image received from an image capturing device, the image being of an environment in which a monitoring target acts;
determining whether an act captured in the image is likely to cause the monitoring target to be exposed to danger, the act including the monitoring target moving towards a preselected location within a preselected range of an object in the environment; and
sending over a network, in accordance with a determination that the act is likely to expose the monitoring target to harm based on the act and a predetermined fitness level of the monitoring target, a notification indicating that the monitoring target is likely to be exposed to danger to at least one of the monitoring target and a third party.

11. The non-transitory computer readable medium according to claim 10, wherein the preselected range correlates to the predetermined fitness level of the monitoring target such that the greater the predetermined fitness level of the monitoring target, the shorter the preselected range is in determining whether the act captured in the image is likely to cause the monitoring target to be exposed to danger.

12. The non-transitory computer readable medium according to claim 10, further includes determining a moving path of the monitoring target, wherein
determining whether an act captured in the image is likely to cause the monitoring target to be exposed to danger is further based on whether the moving path matches the act, and
the predetermined fitness level is one of a plurality of predetermined fitness levels that each fall within a distinct range of a measurable criteria, and the predetermined fitness level is determined based on the measurable criteria obtained for the monitoring target.

13. A monitoring apparatus comprising:
a detector, implemented on one or more processors, that receives an image from an image capturing device, the image being of an environment in which a person acts, and determines whether an act captured in the image is likely to cause the person to be exposed to danger;
an identifying unit, implemented on the one or more processors, that identifies a location in the environment predefined in an environmental map;
a determination unit that determines whether the act is likely to cause harm to the person based on the act, the location in the environment, and a predetermined fitness level of the person; and
a notifying unit, implemented on the one or more processors, that sends over a network, in accordance with the determination that the act is likely to cause the person to be exposed to harm, a notification indicating that the person is likely to be exposed to danger to at least one of the person and a third party, wherein
the act is the person approaching the location or the person coming within a predetermined range of the location, and the fitness level is set based on a walking ability level of the monitoring target.

14. The monitoring apparatus according to claim 13, wherein the act includes the person moving towards a preselected location within a preselected range of an object in the environment.

15. The monitoring apparatus according to claim 13, wherein the act includes the person moving towards a preselected location of an object in the environment.

16. The monitoring apparatus according to claim 13, wherein the predetermined range correlates to the predetermined fitness level of the person such that the greater the walking ability of the person, the shorter the preselected range is in determining whether the act captured in the image is likely to cause the person to be exposed to danger.

17. The monitoring apparatus according to claim 13, wherein
- the determination unit determines a moving path of the person and whether the moving path matches the act,
- the preselected range correlates to the predetermined fitness level of the person such that the greater the predetermined fitness level of the person, the shorter the preselected range is in determining whether the act, matching the moving path, is likely to cause the person to be exposed to danger, and
- the predetermined fitness level is one of a plurality of predetermined fitness levels that each fall within a distinct range of a measurable criteria, and the predetermined fitness level is determined based on the measurable criteria obtained for the person.

* * * * *